US006946485B2

(12) United States Patent
Kloog et al.

(10) Patent No.: US 6,946,485 B2
(45) Date of Patent: Sep. 20, 2005

(54) TREATMENT OF POST-ANGIOPLASTY RESTENOSIS AND ATHEROSCLEROSIS WITH RAS ANTAGONISTS

(75) Inventors: Yoel Kloog, Herzlia (IL); Gad Keren, Kiryat Ono (IL); Jakob George, Tel Aviv-Yafo (IL)

(73) Assignee: Ramot at Tel Aviv University, Ltd. (IL)

( * ) Notice: Subject to any disclaimer, the term of this patent is extended or adjusted under 35 U.S.C. 154(b) by 17 days.

(21) Appl. No.: 10/420,682

(22) Filed: Apr. 22, 2003

(65) Prior Publication Data

US 2003/0203942 A1 Oct. 30, 2003

Related U.S. Application Data

(63) Continuation of application No. 10/023,545, filed on Dec. 18, 2001, now abandoned, which is a continuation-in-part of application No. 09/597,332, filed on Jun. 19, 2000, now Pat. No. 6,462,086.
(60) Provisional application No. 60/140,192, filed on Jun. 18, 1999.

(51) Int. Cl.[7] ............................................. A01N 37/10

(52) U.S. Cl. ........................ 514/532; 514/602; 514/609

(58) Field of Search ............................... 514/532, 602, 514/609

(56) References Cited

U.S. PATENT DOCUMENTS

| 3,910,894 A | 10/1975 | Wah Wat |
| 4,886,916 A | 12/1989 | Onishi et al. |
| 5,580,955 A | 12/1996 | Nur-E-Kamal et al. |
| 5,705,528 A | 1/1998 | Kloog |

FOREIGN PATENT DOCUMENTS

| EP | 0 315 913 B1 | 5/1989 |
| WO | WO 97/30992 | 8/1997 |
| WO | WO 98/02436 | 1/1998 |
| WO | WO 98/38509 | * 9/1998 |
| WO | WO 99/18951 | 4/1999 |

OTHER PUBLICATIONS

Marciano, D. et al, Bioorganic and Medicinal Chemistry Letters, vol. 7, No. 13, pp. 1709–1714, 1997.*
Reif, et al., Hepatology, 1997, 26(4), part 2: 448A (abstract only).
Ohtsuka, et al., Biochim. Biophys. Acta. 1310:223–232 (1996).
Taneja, et al., J. Clin. Invest. 101:921–926 (1998).
Gana–Weisz, et al., Biochem. Biophys. Res. Commun. 239:900–904 (1997).
Marciano, et al., Bioeng. Med. Chem. Lett. 7:1709–1714 (1997).
Paterson immunological Diseases, 3rd Ed. 1400 Little, Brown and Company, Boston (1978).
Lieder, et al. Science 239:181 (1988).
Varela, et al., Immunol. Today 12:159 (1991).
Cohen, et al., Immunol. Today 12:105 (1991).
Lehmann, et al., Clin Immunol Immunopathol 85:202 (1997).
Aharonson, et al., Biochim. Biophys. Acta 1406:40–50 (1998).
Baldari et al., J. Biol. Chem. 268:2693 (1993).
Siegel, et al., Semin Immunol. 3:325 (1991).
Boguski, et al., Nature 366:643–654 (1993).
Cox, et al., Biochim. Biophys. Acta 1333:F51 (1997).
Marshall, Curr. Opin. Cell Biol. 8:197 (1996).
Scheffzek, et al., Science 277:333 (1997).
Haklai, et al., 37:1306–1314 (1998).
Marciano, et al., J. Med. Chem. 38:1267–72 (1995).
Weisz, et al., Oncogene 18:2579–2588 (1999).
Casey, et al., Proc. Natl. Acad. Sci. USA 86:8323.
Hancock, et al., Cell 57:1167 (1989).
Jansen, et al., Proc. Natl. Acad. Sci. U.S.A 96:14019–14024 (1999).
Martin, et al., Crit Rev Clin Lab Sci 32:121 (1995).
Raine, Ann Neurol 36 (suppl.):S61 (1994).
Hafler, et al., Immunol Today 10:104 (1989).
Lublin, Springer Semin Immunopathol 8:197 (1985).
van der Veen, et al., J Neuroimmunol. 21:183 (1989).
Karussis, et al., J. Neurol Sci 153:239 (1998).
Dalakas, Ann Neurol 37 Suppl 1:S2 (1995).
Lisak, Neurology (1988).
Karussis, et al., J. Immunol. 148:1693 (1992).
Diebler, et al., Prep. Biochem. 2:139 (1972).
Barany, et al., Academic Press, NY 2:1 (1980).
Bernard, et al., J Immunol 114:1537 (1975).
Reif, et al., J. Hepatol. 31:1053–1061 (1999).
Niv, et al., J Biol Chem 274:1606–1613 (1999).
Padula, et al., J Immunol 146:879 (1991).
Kuchroo, et al., J Immunol 148:3776 (1992).
Kaladlubowski, et al., Brain Res 184:439–454 (1980).
Shin, et al., Biochim. Biophys. Res. Commun. 224:5–9 (1996).
Marom, et al., J. Biol. Chem. 270:22263–22270 (1995).
Allen, et al., Org. Synthesis 11:580.
Hann, et al., Lab Invest 59:115–125 (1988).
Cliffer, et al., Muscle Nerve 21:1405–1413 (1998).
Shoenfeld, et al., N Engl J Med 311:1019–29 (1984).
Shoenfeld, et al., Immunol Today 10:123–6 (1989).

(Continued)

*Primary Examiner*—Paul J. Killos
(74) *Attorney, Agent, or Firm*—Lerner, David, Littenberg, Krumholz & Mentlik, LLP (57) ABSTRACT

Disclosed are methods for inhibiting Ras activity such as cell proliferation associated with vascular injury such as post-angioplasty restenosis and atherosclerosis. Preferred Ras antagonists are S-trans-trans farnesylthiosalicylic acid (FTS) and structurally related compounds (or analogs) thereof.

49 Claims, 5 Drawing Sheets

OTHER PUBLICATIONS

Ballow, et al., JAMA 278:2008–17 (1997).
Gharavi, et al., Haemostatis 24:204–7 (1994).
Shoenfeld, Curr. Opin. Rheumatol 1:360–8 (1989).
Brey, et al., Ann NY Acad Sci 823:97–106 (1997).
Mendlovic, et al., Proc Natl Acad Sci USA 85:2260–4 (1988).
Shoenfeld, Isr J Med Sci 30:10–8 (1994).
Krause, et al., Int Arch Allergy Immunol 111:355–61 (1996).
Blank, et al., J Autoimmun, 7:441–55 (1994).
Gharavi, et al. , J. Clin Invest 90:1105–9 (1992).
Garcia, et al., Am J Reprod Immunol 37:118–24 (1997).
Blank, et al., Clin Immunol Immunopathol 54:87–97 (1990).
George, et al., Circulation 97:900–6 (1998).
Brey, et al., Lupus, 6:645–51 (1997).
Cameron, et al., Immunology, 59:187–93 (1986).
Dziarski, J Clin Lab Immunol 16:93–109 (1985).
Bernstein, et al., Clin Exp Immunol 93:418–23 (1993).
Kiberd, et al., J Lab Clin Med 124:496–506 (1994).
Woo, et al., Clin Exp Immunol 100:118–25 (1994).
Warner, et al., Arthritis Rheum 37:289–97 (1994).
Henrickson, et al., Arthritis Rheum 37:587–94 (1994).
Merino, et al., J Autoimmun 8:33–45 (1995).
Hori, et al., Dig Dis Sci 38:2195–202 (1993).
Woessner, Arch Biochem Biophys 93:440–447 (1961).
Muller, et al., Exp Pathol 34:229–36 (1988).
Pinzani, et al., J Clin Invest 90:642–646 (1992).
Casini, et al., Gastroenterology 105:245–253 (1993).
Pinzani, et al., J Clin Invest 84:1786–1793 (1989).
Marra, et al., Gastroenterology 112:1297–1306 (1997).
Carloni, et al., Gastroenterology 1996 110:1127–1136.
Schuppan, et al., Cellular and Molecular Aspects of Cirrhosis, Paris: John Libbey Eurotext, Les Editions INSERM 216:115–34 (1992).
Clement, et al., Molecular and Cell Biology of Liver Fibrogenesis, Dordre: Kluwer Academic Publishers, 85–98 (1992).
Ogawa, et al., Am J Pathol 125:611–619 (1986).
Dashti, et al., Eur Surg Res 21:83–91 (1989).
Chieli, et al., Toxicology 31:41–52 (1984).
Liu, et al., Circulation 79:1374–1387 (1989).
Fuster, et al., N. Engl. J. Med. 236:242–250 (1992).
Libby, et al., Circulation 86 (Suppl.) III47–III52 (1992).
Ross, Nature (Lond.), 362:801–809 (1993).
Hanke, et al., Circulation Res. 67:651–659 (1990).
Shi, et al., Circulation 94:1655–1664 (1996).
Andersen, Circulation 93:1716–1724 (1996).
Ridker, et al., Engl. J. Med. 336:973–979 (1997).
Ridker, et al., Circulation 98:731–733 (1998).
Koeing, Eur. Heart J. Suppl. 1:T19–T26 (1999).
Clowes, et al., Lab Invest. 49:327–334 (1983).
Kaitenbach, et al., Eur. Heart J. 6:276–281 (1985).
Nobuyoshi, et al., J. Am. Coll. Cardiol. 12:616–623 (1988).
RITA Trial Participants (1993) Lancet. 341:573–580.
Califf, et al., J. Am. Coll. Cardiol. 17:2B–13B (1991).
Popma, et al., Circulation 84:1426–1436 (1991).
Franklin, et al., Coronary Artery Dis. 4:232–242 (1993).
Teirstein, et al., N. Eng. J. Med 336:1697–1703 (1997).
Condado, et al., Circulation 96:727–732 (1997).
Katz, et al., JOC 18:1380–1402 (1953).
Allen, et al., Org. Synthesis IV:295.
Okachi, et al., J. Med Chem. 28:1772–1779 (1985).
Carmelin, et al., J. Med Chem 29:743–751 (1994).
Tarbell, et al., Am. Soc. 74:48 (1952).
Tarbell, et al., Org. React. 5:193–228 (1949).
Ding, et al., WO/97/30992, CA 127:278213 (Abstract) (1997).
Rebollo, et al., Blood 94:2971–2980 (1999).
Lange–Carter, et al., Science 265:1458–1461 (1994).
Li, et al., Mol. Cell. Biol. 6:5947–54 (1996).
Chatterjee, et al., Glycobiology 7:703–710 (1997).
Kiaris et al., Atherosclerosis 125:47–51 (1996).
Kloog et al., Exp. Opin. Invest. Drugs 8(12):2121–2140 (1999).

* cited by examiner

TREATMENT OF POST-ANGIOPLASTY RESTENOSIS AND ATHEROSCLEROSIS WITH RAS ANTAGONISTS

CROSS-REFERENCE TO RELATED APPLICATIONS

This application is a continuation of U.S. application Ser. No. 10/023,545, filed Dec. 18, 2001, now abandoned, which is a continuation-in-part of U.S. application Ser. No. 09/597,332, filed Jun. 19, 2000, now U.S. Pat. No. 6,462,086, which claims priority under 35 U.S.C. §119(e) from U.S. application Ser. No. 60/140,192, filed Jun. 18, 1999. The contents of these two applications are hereby incorporated herein by reference in their entireties.

FIELD OF THE INVENTION

The present invention relates to the inhibition of the onset of or the treatment of non-malignant diseases, and particularly diseases having pathologies involving Ras-induced proliferation of cells.

BACKGROUND OF THE INVENTION

Autoimmune diseases include disorders involving dysfunction of the immune system, which mediates tissue damage. Any organ may be affected by such processes through precipitation of immune complexes, cellular immunity, or inappropriate generation or action of immunohormones such as cytokines. Epidemiologically, autoimmune diseases are significant because of the numbers of patients that they affect and the serious morbidity and mortality that they cause. Common chronic systemic diseases in this group include diabetes mellitus, thyroid disease, rheumatoid arthritis, systemic lupus erythmatosus (SLE), primary antiphospholipid syndrome (APS), and a variety of diseases that affect the central nervous system. Neurological autoimmune diseases include disorders specific to the nervous system such as myasthenia gravis, Lambert Eaton myasthenic syndrome, Guillain-Barre syndrome, polymyositis, and multiple sclerosis. In addition, there are neurological complications of the systemic autoimmune diseases. Factors predisposing to autoimmune diseases include genetic predisposition and environmental agents such as certain infections and pharmaceutical products. Such factors result in pathological activation of the immune response in susceptible individuals, which is generally controlled by T lymphocytes (T cells). The activation of T cells and B subtypes, involves a complex interaction of cell surface receptors resulting in equally complex signal transduction pathways which eventually affect gene regulation. Full activation of lymphocytes requires parallel stimulation of several signal transduction pathways. See Ohtsuka et al., Biochim. Biophys. Acta. 1310:223–232 (1996).

Although there is growing understanding about the function of T cells in the immune response, this knowledge has not explained the basis of most autoimmune diseases. There are still questions to be resolved such as how tolerance to self in normal individuals is maintained; how tolerance is broken in autoimmunity; and which autoantigens trigger the immune system to produce specific diseases. A recent review by V. Taneja and C. S. David (J. Clin. Invest. 101:921–926 (1998)) provides an overview of important issues in this field and emphasizes how the generation of transgenic mice expressing functional HLA molecules is important for understanding the function of certain molecules in the induction of autoimmune disease, as well as circumvention of the xenogenic barrier. Regardless of the mechanisms involved in induction of autoimmune disease or the rejection of grafts, the common pathway for these events includes activation of a relatively small number of T lymphocytes.

Several immunosuppressive and immunomodulating treatments have been tested and subsequently applied in the treatment of autoimmune diseases. Gana-Weisz, M., HaMai, R., Marciano, D., Egozi, Y., Ben-Baruch, G., and Kloog, Y. The Ras antagonist S-farnesylthiosalicylic acid induces inhibition of MAPK activation. Biochem. Biophys. Res. Commun. 1997; 239: 900–904; Marciano, D., Aharonson*, Varsano, T., Haklai, R., and KO, Y. Novel inhibitors of the prenylated protein methyltransferase reveal distinctive structural requirements. Bioerg. Med. Chem. Lett. 1997; 7, 1709–1714; Paterson P. Y. (1978) The demyelinating diseases: clinical and experimental studies in animals and man. In: Immunological Diseases, 3rd Edition, (ed. by M. Smater, N. Alexander, B. Rose, W. B. Sherman, D. W. Talmage and J. H. Vaughn) p. 1400. Little, Brown and Company, Boston.

The main drawback of immunosuppressive modalities is that the induction of generalized suppression of all T-cells and immune functions is associated with long-term and cumulative side effects. In addition, it is now believed that broad suppression of immune cells may also cancel or neutralize the potential beneficial effects of down-regulatory cells such as suppressors and suppresor inducers or cytokines such as IL-10, on the autoimmune lymphocytes. Karussis, et al., supra; Gana-Weisz, et al., supra, Lieder, O., T. Reshef, E. Berauud, A. Ben-Nun, and I. R. Cohen. 1988, Anti-idiotypic network induced by T cell vaccination against experimental autoimmune encephalomyelitis, *Science* 239:181; Varela, F. J., and A. Coutinho, 1991, Second generation immune networks, *Immunol. Today* 12:159; Cohen, I. R., and D. B. Young. 1991, Autoimmunity, microbial immunity and the immunological homunculus, *Immunol. Today* 12:105; Lehmann, D., D. Karussis, R. Mizrachi-Koll, A. S. Linde, and O. Abramsky, 1997, Inhibition of the progression of multiple sclerosis by linomide is associated with upregulation of CD4+/CD45RA+ cells and downregulation of CD4+/CD45RO+ cells, *Clin Immunol Immunopathol* 85:202.

Therefore, current approaches for the treatment of autoimmune diseases advocate the use of immunomodulators or specific immunosuppressing medications. The goal of such research is specific suppression of only the lymphocytes with the autoimmune potential. The search for such specific suppressors is a formidable challenge, particularly considering the complex networks of signal transduction pathways associated with lymphocyte growth and differentiation, where many such pathways are common to all lymphoid lineages and to other cells.

In addition to autoimmune disease, there are several other diseases in which proliferation of normal cells other than T-cells constitutes part of the pathology.

SUMMARY OF THE INVENTION

An aspect of the present invention is directed to a method of inhibiting Ras activity associated with vascular injury which entails administration of a Ras antagonist in an amount effective to inhibit the Ras activity. In a preferred embodiment, the present invention is directed to a method of inhibiting Ras activity associated with post-angioplasty restenosis, by administering to a patient suffering from or at risk of restenosis, a Ras antagonist in an amount effective to inhibit the Ras activity. In this embodiment, a primary targeted activity of Ras in connection with restenosis is the proliferation of vascular smooth muscle cells. In another embodiment, the present invention is directed to a method for inhibiting Ras activity in a patient with atherosclerosis or a patient at risk for atherosclerosis. The patient is administered a Ras antagonist in an amount effective to inhibit the Ras activity.

Common to vascular injury is Ras. This protein becomes activated by a series of biochemical events after it binds or docks to a particular site on the inner surface of the cell membrane. The activation of Ras then leads to another series of inter-related biochemical reactions or signal transduction cascades that ultimately produce cell growth and division. The Ras antagonists of the present invention are believed to inhibit Ras activity by inhibiting or reducing the binding of Ras to the cell membrane, which in turn reduces or inhibits the unwanted cell proliferation.

Preferred Ras antagonists include farnesyl thiosalicylic acid (FTS) and structurally related compounds or analogs thereof, which are believed to function by displacing or dislodging Ras from its membrane anchor. Thus, in these respects, the invention may also be described in terms of a method of displacing or dislodging Ras from its cell membrane anchor in a mammal suffering from vascular injury, by administering a Ras antagonist in an amount effective to displace or dislodge Ras from its cell membrane anchor. Ras antagonists may be administered parenterally or orally. In a particularly preferred embodiment, the Ras antagonist is formulated for oral or parenteral administration by complexation with cyclodextrin or as nanocrystals.

FTS has been shown to affect the growth of cancers in animals mediated by oncogenic forms of Ras, including melanomas and lung, colon, pancreatic, uterine and Merkel cell cancers. The results of these experiments showed that FTS achieved greater than 90% reduction in cancer cell growth in some cases without significant toxic effects associated with standard cancer chemotherapy. The results also showed that similar dosages of FTS used in cancer treatment had very little, if any, effect on normal cells. See Aharonson, et al., Biochim. Biophys. Acta 1406:40–50 (1998). It was known that the proliferation of normal cells associated with various non-malignant diseases (e.g., T-cells associated with various autoimmune diseases, stellate cells associated with cirrhosis and smooth muscle cells associated with post angioplasty restenosis) was mediated at least in part by normal or non-oncogenic Ras. Still, it was not expected that FTS and similarly active compounds could be used to achieve a therapeutic benefit in patients afflicted with diseases characterized by proliferations of normal cells.

The methods of the present invention offer several advantages over current immunosuppressive and immunomodulatory treatment modalities. They are generally non-cytotoxic to all dividing cells, non-toxic at therapeutically effective doses, and do not result in general immunosuppression.

BRIEF DESCRIPTION OF THE FIGURES

FIGS. 1A and B are bar graphs showing that FTS suppresses early and advanced lesions in apoE deficient chow fed (A) and high fat diet fed (B) mice.

DETAILED DESCRIPTION OF THE INVENTION

The methods of the present invention are directed to the treatment of non-malignant diseases, pathological states or other disorders involving vascular injury that feature or otherwise include Ras activity such as Ras-induced proliferation of cells. One example of vascular injury is post-angioplasty restenosis. Here, the insertion of an intra-arterial stent causes damage, release of growth factors and proliferation of normal smooth muscle cells.

Atherosclerosis is another example of a non-malignant disease state characterized by abberant Ras activity. It involves uninhibited accumulation of lipids in the vessel wall resulting in considerable morbidity and mortality. Although conclusive data is not yet available, it is becoming apparent that no single mechanism is solely responsible for the development of the atherosclerotic plaque, but rather an interplay of factors. See, Ross, N. Eng. J. Med. 340:115–126 (1999). In the recent years, agrowing body of evidence has been presented supporting the participation of the immune system in the initiation and progression of atherosclerosis, Ross, supra; Libby, et al. Lab. Invest. 64: 5–11 (1991). This notion is based on the idea that atherosclerosis is a form of a chronic inflammatory state that involves interaction among endothelial cells, macrophages, T lymphocytes and smooth muscle cells, Ross, supra. According to the currently acceptable views and without intending to be bound by any particular theory of operation, turbulent flow within the arterial system imposes stress on the vessel walls. Consequently, expression of endothelial adhesion molecules ensues, resulting in recruitment of monocytes that transform to macrophages. These macrophages which express scavenger receptors initiate an unregulated intake of modified lipoproteins (oxidized LDL) that culminate in plaque formation, Ross, supra. Many of the diverse signals triggered by receptors that are involved in the atherosclerotic process would require intact Ras pathways, which play a key role in the control of cell growth and differentiation, cell migration and adhesion and cell survival, Boguski et al., Nature (London) 366:643–654 (1993); Rebollo et al., *Blood* 94:2971–2980 (1999); Lange-Carter et al., Science 265:1458–1461 (1994). Thus, aberrant Ras functions contribute to the atherosclerotic process by analogy to the cases of human tumors that harbor activated ras genes or overexpress receptors that activate Ras. In many human tumors, active Ras provides not only growth signals but also strong survival signals and migration potential. A number of experiments also support the direct involvement of active Ras in atherosclerosis. Shear forces resulting from turbulent flow and oxidative stress are contributory, possibly essential, to atherogenesis and have been shown to activate Ras, Li et al., Mol. Cell. Biol. 6:5947–54 (1996). Moreover, oxidized LDL (oxLDL), considered crucial in atherogenesis, has been shown to induce Ras activation in smooth muscle cells, Chatterjee et al., Glycobiology 7:703–710 (1997).

For Ras to be activated (i.e., turned on) to stimulate the regulatory cascades, it must first be attached to the inside of the cell membrane. Ras antagonist drug development aimed at blocking the action of Ras on the regulatory cascades has focused on interrupting the association of Ras with the cell membrane, blocking activation of Ras or inhibiting activated Ras. The details of the approaches to development of Ras antagonists are reviewed in Kloog et al., Exp. Opin. Invest. Drugs 8(12):2121–2140 (1999). Thus, by the term "Ras antagonist," it is meant any compound or agent that targets one or more of these phenomena so as to result in inhibition of Ras activity e.g., that results in cell proliferation.

Preferred Ras antagonist is represented by formula I:

wherein
$R^1$ represents farnesyl, geranyl or geranyl-geranyl;
$Z$ represents C—$R^6$ or N;
   $R^2$ represents H, CN, the groups $COOR^7$, $SO_3R^7$, $CONR^7R^8$, COOM, $SO_3M$ and $SO_2NR^7R^8$, wherein $R^7$ and $R^8$ are each independently hydrogen, alkyl or alkenyl, and wherein M is a cation;
   $R^3$, $R^4$, $R^5$ and $R^6$ are each independently hydrogen, carboxyl, alkyl, alkenyl, aminoalkyl, nitroalkyl, nitro, halo, amino, mono- or di-alkylamino, mercapto, mercaptoalkyl, axido, or thiocyanato;
   X represents O, S, SO, $SO_2$, NH or Se; and
   the quaternary ammonium salts and N-oxides of the compounds of formula (I) wherein Z is N.

These compounds represent farnesyl-thiosalicylic acid (FTS) e.g., S-trans, trans-FTS) and its analogs. In embodiments wherein $R^2$ represents H, $R^3$ is preferably a carboxyl group. The structures of FTS and two preferred analogs are as follows:
(i) FTS:

(ii) 2-chloro-5-farnesylaminobenzoic acid (NFCB):

(iii) farnesyl thionicotinic acid (FTN):

Yet other FTS analogs embraced by formula I include 5-fluoro-FTS, 5-chloro-FTS, 4-chloro-FTS and S-farnesyl-thiosalicylic acid methyl ester (FMTS). Structures of these compounds are set forth below.

5-Cl-FTS

4-Cl-FTS

5-F-FTS

FMTS

A particularly preferred agent is FTS. This compound destabilizes the proper attachment of Ras to the cell membrane which is promoted by the Ras carboxy terminal S-farnesyl cysteine required for Ras signaling. FTS and other compounds of the present invention mimic Ras anchorage moieties and disrupt the interactions of Ras with the cell membrane in living cells without being cytotoxic. Without intending to be bound by any particular theory of operation, it is believed that its mechanism of action involves a dual effect on membrane Ras where initially (within 30 min) FTS releases Ras from constraints on its lateral mobility which is followed by release of Ras into the cytoplasm from its isoprenoid dependent anchorage proteins, and then by Ras degradation. The reduced amount of Ras and the altered membrane mobility of Ras in FTS-treated fibroblasts and human tumor cells are then manifested in the inhibition of Ras-mediated signaling to the mitogen activated protein kinase (MAPK) Erk. This is also believed to explain why FTS inhibits proliferation of Ras-transformed cells and inhibits the mitogenic stimuli of T-cell antigens and of growth factors such as thrombin and EGF, PDGF and FGF.

Compounds useful in the present invention are further disclosed in Marciano, et al., 1995, J. Med. Chem. 38, 1267; Haklai, et al., 1998, Biochemistry 37, 1306; Casey, et al., Proc. Natl. Acad. Sci. USA 86, 8323; Hancock et al., 1989, Cell 57, 1167 and Aharonson, et al., 1998, Biochim. Biophys. Acta. 1406, 40.

Other Ras antagonists useful in the present invention may be identified by using the cell free membrane assays and cellular assays described in WO 98/38509. This patent publication describes several assay systems designed to determine the ability of a candidate agent to dislodge activated Ras from cell membranes. In general, the assay material that contains specific membranes having a known and detectable quantity of Ras anchored thereto is exposed to the candidate agent. The assay material is then separated into a membrane fraction containing the membranes and a cytosolic fraction of a balance of the material remaining after the specific membranes are removed. A fraction of the known quantity of the labeled Ras contained in the membrane and cytosolic fraction is determined as a measure of the ability of the candidate agent to disrupt membrane association of Ras. A particularly convenient source of activated Ras-anchored membranes is membranes isolated from Ras transformed cancer cells such as Panc-1 cells. The Ras remaining in the membranes after exposure to a candidate agent can be measured by standard immuno-assays using anti-Ras antibodies.

Yet other Ras antagonists useful in the present invention may be identified in accordance with the procedures described in commonly owned application no. PCT/IL01/00918, filed Oct. 1, 2001, entitled Isoprenoid-dependent Ras anchorage (IDRA) proteins, which claims priority from commonly owned provisional Patent Application No. 60/237,858. This patent application describes several assays, designed to identify canidate agents that will disassociate activated Ras from one or more anchor proteins with which Ras proteins associate in the cell membrane. In certain assays, cells in which either or both Ras or anchor protein are labelled with GFP or another protein tag are visualized. The ability of a candidate drug to disrupt Ras/anchor membrane protein interactions is detected by a change in the location of Ras and/or the anchor protein in the cell. Examples of the change and location include movement from the cytoplasm to the cell membrane, from the cell membrane to cytoplasm, and from membrane to a cellular compartment other than the cell membrane. In the cell-free variant of these assays, the candidate agent disrupts the interaction of Ras with its anchor(s), the dimerization of Ras, the dimerization of the anchor or the interaction of Ras with Raf protein.

The Ras antagonists or agents of the present invention tend to be substantially insoluble in water and saline solutions such as PBS. Thus, in one embodiment, the agents are salified [e.g., an $Na^+$, $K^+$ or $NH^+$ form] and formulated with an organic solvent such as alkyl gallates and butylated hydroxyanisole containing lecithin and/or citric acid or phosphoric acid. In these formulations, the alkyl gallate, etc., is present in an amount of from 0.02% to about 0.05%, and the citric or phosphoric acid is present in an amount of about 0.01%. These formulations are suitable for parenteral administration.

In addition to being insoluble in water, various Ras antagonists such as FTS and its analogs are not active when administered orally. It is believed that the standard crystals of the drug do not dissolve in the gastrointestinal tract. In one embodiment of the present invention, both of these shortcomings are overcome by formulating the agent in cyclodextrin. This technology is the subject of U.S. Pat. Nos. 5,681,828 and 5,935,941. Cyclodextrins are a group of compounds consisting of, or derived from, the three parent cyclodextrins—alpha-, beta- and gamma-cyclodextrins. Alpha-, beta- and gamma-cyclodextrins are simple oligosaccharides consisting of six, seven or eight anhydroglucose residues, respectively, connected to macrocyles by alpha (1 to 4) glycosidic bonds. Each of the glucose residues of a cyclodextrin contains one primary (O6) and two secondary hydroxyls (O2 and O3) which can be substituted, for example, methylated. Many cyclodextrin preparations in practical use are mixtures of chemically individual derivatives in which only a part of hydroxy groups were substituted and which differ in number and position of these substituents.

Cyclodextrins solubilize insoluble compounds into polar media by forming what is known as an inclusion complex between the cyclodextrin and the insoluble compound; cyclodextrin solubilization power is directly proportional to the stability of the complex. Inclusion complexes are non-covalent associations of molecules in which a molecule of one compound, called the host, has a cavity in which a molecule of another compound, called a guest is included. Derivatives of cyclodextrins are used as the hosts, and the insoluble compound is the guest.

In this invention, many different cyclodextrin derivatives may be used. These include several types of mixtures of partially methylated cyclodextrins. One type is a commercial preparation (Wacker Chemie, Beta W7M1.8) in which the methyl groups are about equally distributed between the primary and secondary hydroxyls of glucopyranose residues; it is abbreviated as RAMEB. A second type has methyls predominantly on the secondary hydroxyls. These derivatives are described in U.S. Pat. No. 5,681,828. A third type of methylated cyclodextrins is formed by those cyclodextrin derivatives or their mixtures that have more than half of their secondary hydroxy groups (i.e., O2 and O3) methylated. Other mixtures of cyclodextrin derivatives are partial 2-hydroxypropyl ethers, abbreviated as HPACD, HPBCD or HPGCD for derivatives of alpha-, beta- and gamma-cyclodextrins, respectively.

To potentiate the formation of inclusion complexes between the cyclodextrins and the Ras antagonists, highly methylated cyclodextrins may be covalently or non-covalently complexed with less substituted cyclodextrins.

Briefly, the Ras antagonist is salified and dissolved in an appropriate solvent, and then added to a solution of methylated cyclodextrin in PBS. The result of the solution is sterilized and then the solvent is removed. To prepare a formulation suitable for oral administration, the resultant cyclodextrin/FTS complex is mixed with a suitable binder and then pressed into buccal tablets, oral tablets or capsules. The buccal tablets dissolve when held in the mouth against the mucus membrane. It is believed that as the tablet dissolves, the cyclodextrin particles touch the membrane and the drug is released and is passed across the membrane of the mouth into the bloodstream. In other embodiments, the cyclodextrin/Ras antagonist complex is reconsituted into solutions suitable for oral or parenteral (e.g., intravenous or subcutaneous) administration.

An alternative method of formulating the Ras antagonist of the present invention such as FTS that are insoluble in water, is to convert the crystals of drug, which are several $\mu$m in diameter, into crystals with a diameter in nanometers. The production of nanocrystals may be accomplished by commercially known procedures such as ones developed by Elan Pharmaceutical Technologies (see e.g., U.S. Pat. Nos. 4,610,875 and 5,641,515). See also U.S. Pat. No. 5,145,684. Such nanocrystals are suitable for oral, parenteral and inhalation routes of administration. Nanocrystal formulations enchance bioavailability, net onset of drug action, improved drug proportionalities, reduce fed-fasted effects, and increase the drug loading without increasing toxicity.

Clinical effects may be achieved with dosages of the Ras antagonist of about 1 mg/kg per day. In general, however, amounts of the Ras antagonist effective for the present purposes, which are treatment of the patients and inhibition of Ras activity, e.g., Ras-mediated cell proliferation, range from about 5 mg/kg every other day to about 5 mg/kg per day. The response may be magnified by increasing the dose up to about 20 mg/kg per day in a single treatment as well as by increasing the frequency of treatment. Alternatively, from about 20 to about 80 mg/kg can be administered once weekly.

Timing of the administration of the Ras antagonist is important to the extent that it is in circulation so as to be in contact with the cells before or during proliferation. In the case of restenosis, for example, the antagonist is preferably administered prophylactically such as by way of i.v. infusion at about the time of angioplasty. Administration is continued for about 14 days. In addition to i.v. administration, the agent may be formulated into a transdermal preparation such as a cream, gel or patch, or in the form of a prodrug, optionally complexed with cyclodextrin. In the case of atherosclerosis, it is preferable to administer the Ras antagonist before or during accumulation of lipid in the artery. Atherosclerotic patients, or those at risk can be administered the Ras antagonists by way of an oral preparation on a daily basis. Administration is preferably continued for a year. The present invention will now be described by way of the following examples. These examples demonstrate the efficacy of a Ras antagonist of the present invention to inhibit or reduce the proliferation of normal cells associated with various disease states including animal models of atherosclerosis and restenosis. They are presented solely for purposes of illustration, and are not intended to limit the invention in any way. For ease of reading, citations of the referenced scientific publications are listed at the end of each example.

EXAMPLE 1

Functional Inhibition of Ras by FTS Attenuates Atherosclerosis in Apolipoprotein E Knockout Mice The following example demonstrates the efficacy of Ras antagonist of the present invention, FTS, to inhibit or reduce early and advanced atherosclerotic lesions. The experiments were conducted on atherosclerosis-prone mice deficient in apolipoprotein E and which were fed normal and high-fat diets.

Methods

Animals

Apo-E deficient mice on a C57BL/6 background (24–25) were purchased from the Jackson Laboratories and grown at the local animal house. Mice were either fed normal chow-diet containing 4.5% fat by weight (0.02% cholesterol) or a Western-type diet containing 42% of calories from fat, 43% from carbohydrates, 15% from protein (TD 96125, Harlan Teklad).

Experimental Design

In the first experiment, the effect of FTS was studied on fatty streak formation (early atherosclerosis) in apoE mice. For this purpose, 4 week-old male apoE mice were injected I.P. with FTS (5 mg/Kg weight) 3 times a week for 6 weeks and fed a normal chow diet. Upon sacrifice, plasma was obtained for anti-oxLDL antibody level measurement and hearts were removed for estimation of lesion size and plaque composition.

In the second experiment, the effect of FTS was studied on advanced atherosclerotic plaque development. For this purpose, 4 week-old apoE mice were injected I.P. with FTS, or a control vehicle employing the same protocol, yet they were fed a high fat diet for 10 weeks. Upon sacrifice similar measurements were performed as in the first experiment and spleen cells were obtained for assessment of proliferation in the presence of oxLDL.

Lipid Profile.

Total plasma cholesterol and triglyceride levels were determined using an automated enzymatic technique (Boehringer Mannheim, Germany).

Splenocyte Proliferation Assays.

Splenocytes ($1\times10^6$ cells per ml) were incubated in triplicates for 72 h in 0.2 ml of culture medium in microtiter wells in the presence or in the absence of 10 μg/ml mouse oxLDL for 72 hrs. Proliferation was measured by the incorporation of [$^3$H] thymidine into DNA during the final 12 h of incubation as described previously[26].

Detection of Anti-oxidized-LDL Antibodies and Isotypes by ELISA.

Ninety-six well polystyrene plates (Nunc Maxisorp, Denmark) were coated with either ox-LDL (at concentration of 10 μg/ml in PBS) or native LDL (both from humans) overnight at 4° C. Next steps were carried out as described previously (27). IgG isotypes were determined employing an ELISA kit (Southern-Biotechnology).

Measurement of Ras Expression

Levels of Ras protein content were determined in homogenates of aortas obtained from FTS treated mice or controls, employing anti-pan Ras antibodies (PanRas Ab03, Santa Cruz) as previously described (11).

Aortas were homogenized (10% w/v) in cold homogenization buffer containing 150 mM NaCl, 50 mM Tris-HCl pH 7.6, 1 mM dithiothriethol, 5 μg/ml leupeptine, 5 μg/ml pepstatine, 1 mM benzamidine, 1 mM phenylmethylsulfonyl fluoride, 5 units/ml aprotinine and 20 mM $MgCl_2$. The nuclei and the cell debris were then removed by a 10-min 1000×g spin. The resulting supernatant was used for assays. Samples containing 25 μg proteins were used for the determination of total Ras protein (11). Proteins were separated by 12.5% sodium dodecyl sulfate polyacrylamide gel electrophoresis (SDS-PAGE) (mini-gel) and blotted onto nitrocellulose paper. The paper was blocked with 1.5% skim milk in Tris-buffered saline pH 7.6 (containing 0.05% Tween-20 and 150 mM NaCl) overnight, then incubated for 1.5 h with 1:2000 dilution of Pan-Ras Ab in the same buffer. Immunoblots were then incubated for 1 h with 1:7500 dilution of anti mouse IgG horseradish peroxidase conjugate and subjected to enhanced chemiluminescence (ECL) assays. Bands were quantified by densitometry on a BioImaging System 202D System (Dynco-Renium, Jerusalem) using Tina 2.0 software (Ray Tests).

Determination of Active Ras in Aortic Samples from FTS or Control Treated Mice.

The above noted preparations of the aortas (500 μg protein) were adjusted to 0.5% NP-40 and used for the determination of the levels of active GTP bound Ras (reference 28) as follows. The Ras binding domain of human c-Raf-1 (RBD) fused to glutathione-S-transferase (GST) in the expression vector pGEX-2T was prepared in DH-10B E.coli cells. The bacterial lysate was rotated 30 min at 4° C. with glutathione-agarose beads (Sigma) in the homogenization buffer containing NP-40. The beads were then washed with the same buffer and mixed with the above aorta preparation. Samples were then rotated 30 min at 4° C. The active Ras was then precipitated and washed. SDS sample buffer was then added to the precipitated Ras-GTP and the apparent amount of the Ras was determined by immunoblotting with the Pan-Ras Ab as detailed above.

Assessment of Atherosclerosis.

Quantification of atherosclerotic fatty streak lesions was done by calculating the lesion size in the aortic sinus (29). Briefly, the heart and upper section of the aorta were removed from the animals and the peripheral fat cleaned carefully. The upper section was embedded in OCT medium and frozen. Every other section (10 $\mu$m thick) throughout the aortic sinus (400 $\mu$m) was taken for analysis. Sections were evaluated for fatty streak lesions after staining with oil-red O. Lesion areas per sections were counted using a grid by an observer unfamiliar with the tested specimen.

Immunohistochemistry.

Immunohistochemical staining for T-cells (CD3), T cell activation marker (IL-2 receptor), macrophages (Mac-1), NFkB and VCAM-1 were performed on aortic sinus 5 $\mu$m thick frozen sections (26). The sections were fixed for 4 min in methanol at −20° C. followed by 10 min incubation with ethanol at −20° C. The sections were then blocked with non-immune goat serum for 15 min. at room temperature followed by incubation with CAS blocking reagent for 30 min. at room temperature. Subsequently, the rat-monoclonal anti-mouse antibodies were added for 1 hr at room temperature. After washings, affinity purified biotinylated rabbit anti-rat IgG antibodies (Jackson) were added for 30 min at room temperature. After washings, the slides were incubated with 0.3% $H_2O_2$, followed by additional rinses and incubation with streptavidin-peroxidase conjugate for 30 min at room temperature. After washings, the slides were developed with 3 amino-9-ethylcarbonasole (AEC) substrate (Dako) for 15 min. Sections were counterstained with hematoxylin. Spleen sections were used as a positive control. Staining in the absence of 1st or 2nd antibody were used as a negative control. Positive cells were counted by 2 pathologists, blinded to the study protocol, and averaged. VCAM-1 was evaluated by morphometry as previously described (26).

Statistical Analysis

All parameters between the groups were evaluated by the student's t-test. P<0.05 was considered statistically significant. Results are expressed as mean±SEM unless otherwise specified in the text.

Results

FTS Does Not Influence Lipid Profile

Treatment of chow fed mice with FTS did not appear to influence total cholesterol levels (mean levels of 258±61 mg/dl) in comparison with control treatment (212±60 mg/dl; p=n.s). Similarly, total cholesterol levels were not significantly different in the FTS and control treated mice fed a Western diet (870±252 mg/dl vs. 870±185 mg/dl, respectively; p=n.s). FTS administration in both experiments did not affect triglyceride levels (data not shown).

FTS Attenuates Early and Advanced Atherosclerotic Lesions

Figure 1:
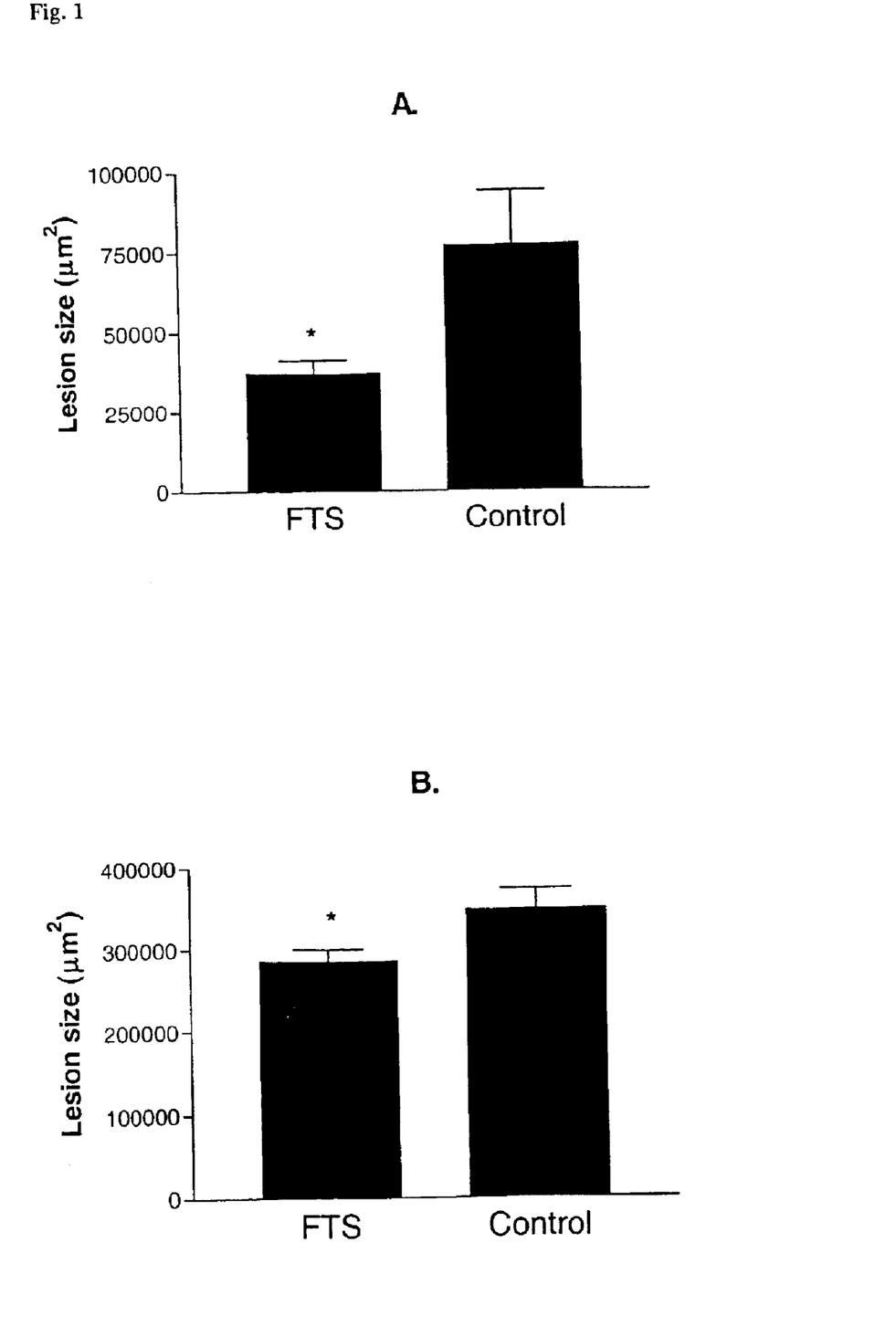

In the first experiment early atherosclerotic lesions were significantly attenuated (a 52% reduction) by treatment with FTS (mean aortic lesion size of 37000±4300 $\mu m^2$) in comparison with controls (77000±17000 $\mu m^2$; p<0.01)(FIG. 1A; photo not shown). Although less pronounced, FTS reduced the more advanced plaques induced by high fat diet feeding (mean lesion size of 285000±15300 $\mu m^2$) as compared with control group (348000±25000 $\mu m^2$ in the control group; p<0.05)(FIG. 1A; photo not shown). This was equivalent to a 28% reduction.

The Effect of FTS on Ras Expression and Activation, in-vivo.

Figure 2:
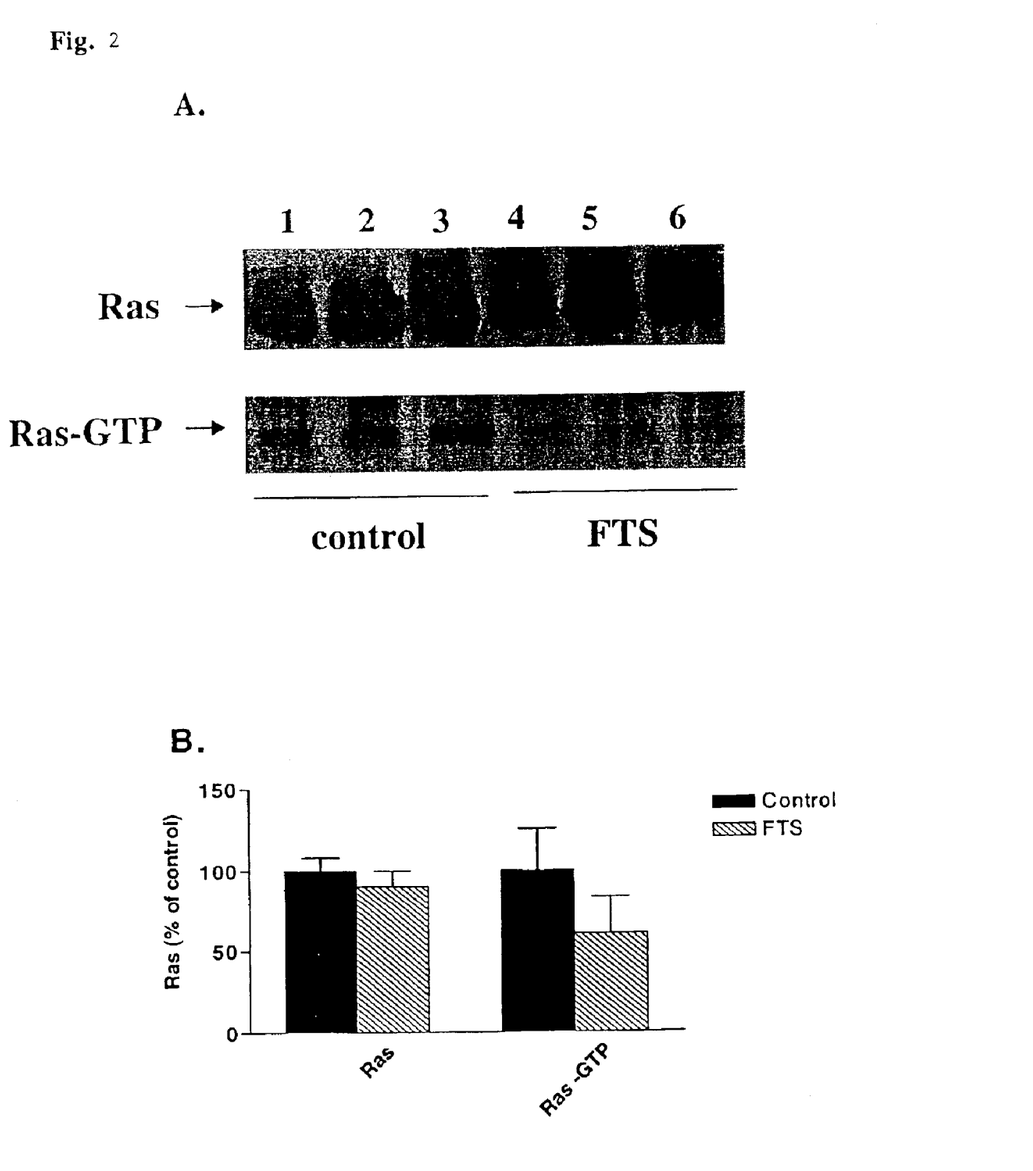
FIG. 2A is a photograph of an immunoblot with Pan-Ras Antibody showing amounts of total Ras (upper panel) and Ras-GTP (lower panel) in aortas from FTS-treated and control mice.
FIG. 2B is a bar graph showing data from a densitometric analysis of aorta samples obtained from 8 control and 6 FTS-treated mice.

To determine whether Ras expression was influenced by FTS treatment, we evaluated Ras protein content in aortas from FTS treated mice as compared with controls. Total Ras protein content did not differ in atheromatous aortas from FTS treated mice in comparison with non-treated (FIG. 2A). To evaluate whether active Ras was diminished due to treatment, we evaluated Ras-GTP content and found it reduced by 40%, in aortas of mice treated with FTS as compared with controls (FIG. 2B).

FTS Reduces Cellular and Humoral Immune Responses to Oxidized LDL

Figure 3:
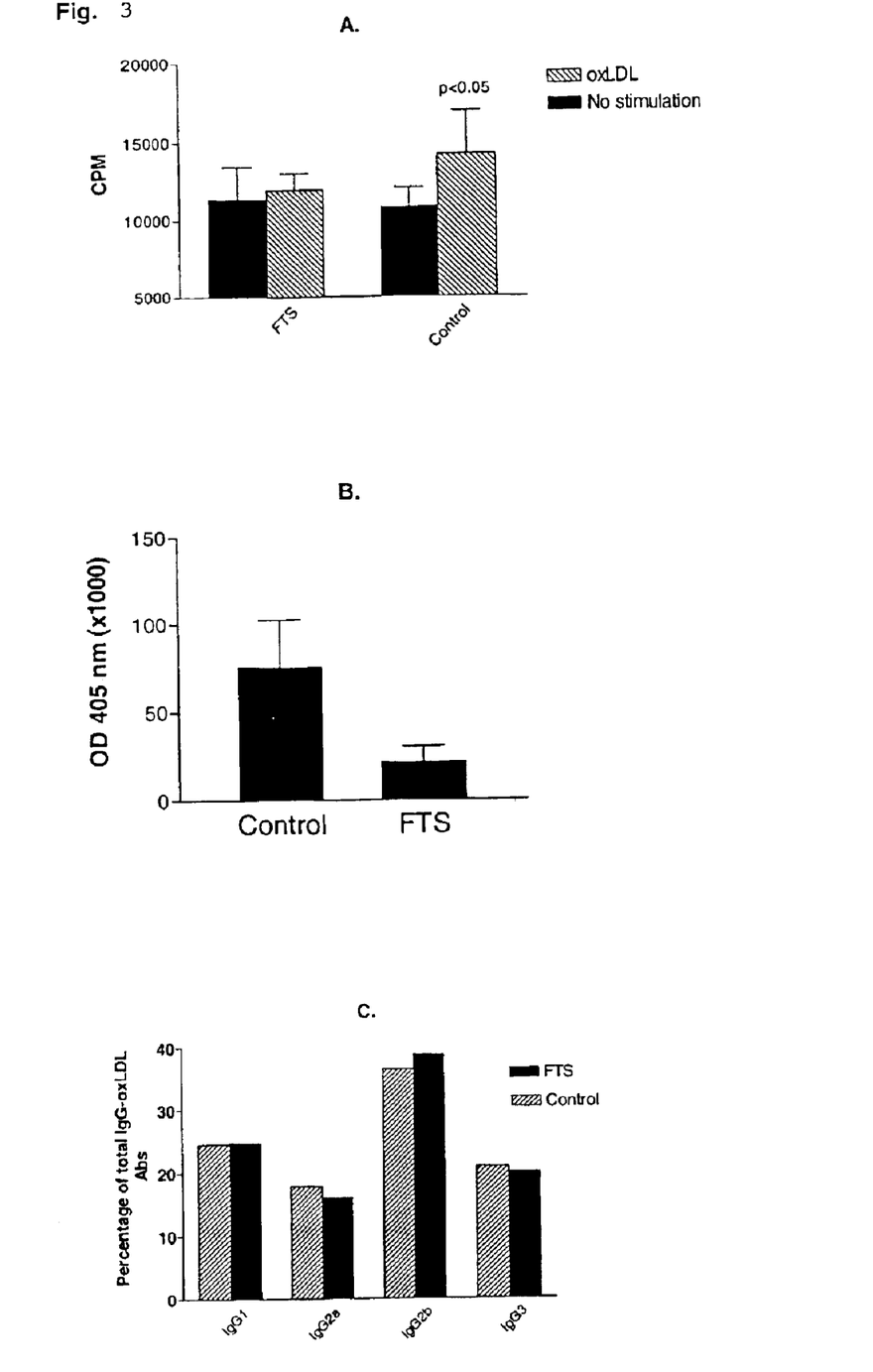
FIGS. 3A, 3B and 3C are bar graphs showing that FTS reduces cellular and humoral immune responses to oxLDL in mice, wherein FIG. 3A expresses the result in CPM, FIG. 3B expresses the results in optical density (OD 405 nm(× 1000), and FIG. 3C shows anti-oxLDL isotype class distribution as a fraction of total IgG-oxLDL binding as evaluated by ELISA.

Next, we explored the effect of anti-Ras treatment on the cellular and humoral immune response to oxLDL, known to prevail in atherosclerotic apoE-deficient mice. Basal proliferative response of splenocytes from FTS treated mice did not differ from control treated animals (FIG. 3A). However, when primed with oxLDL, no significant reactivity was evident in FTS treatment, whereas a 24% (p<0.05) increase in thymidine uptake was obtained in control treated mice (FIG. 3A). Splenocytes from FTS or control treated mice did not differ with regard to their concavaline A induced proliferation (data not shown).

Similar to the effects on cellular immunity, IgG anti-oxLDL antibody levels were reduced in mice treated with FTS as compared with levels in the controls (mean OD of 0.22±0,08 Vs 0.76±0.3; p<0.05)(FIG. 3b).

FTS Does Not Modify Plaque Composition.

Figure 4:
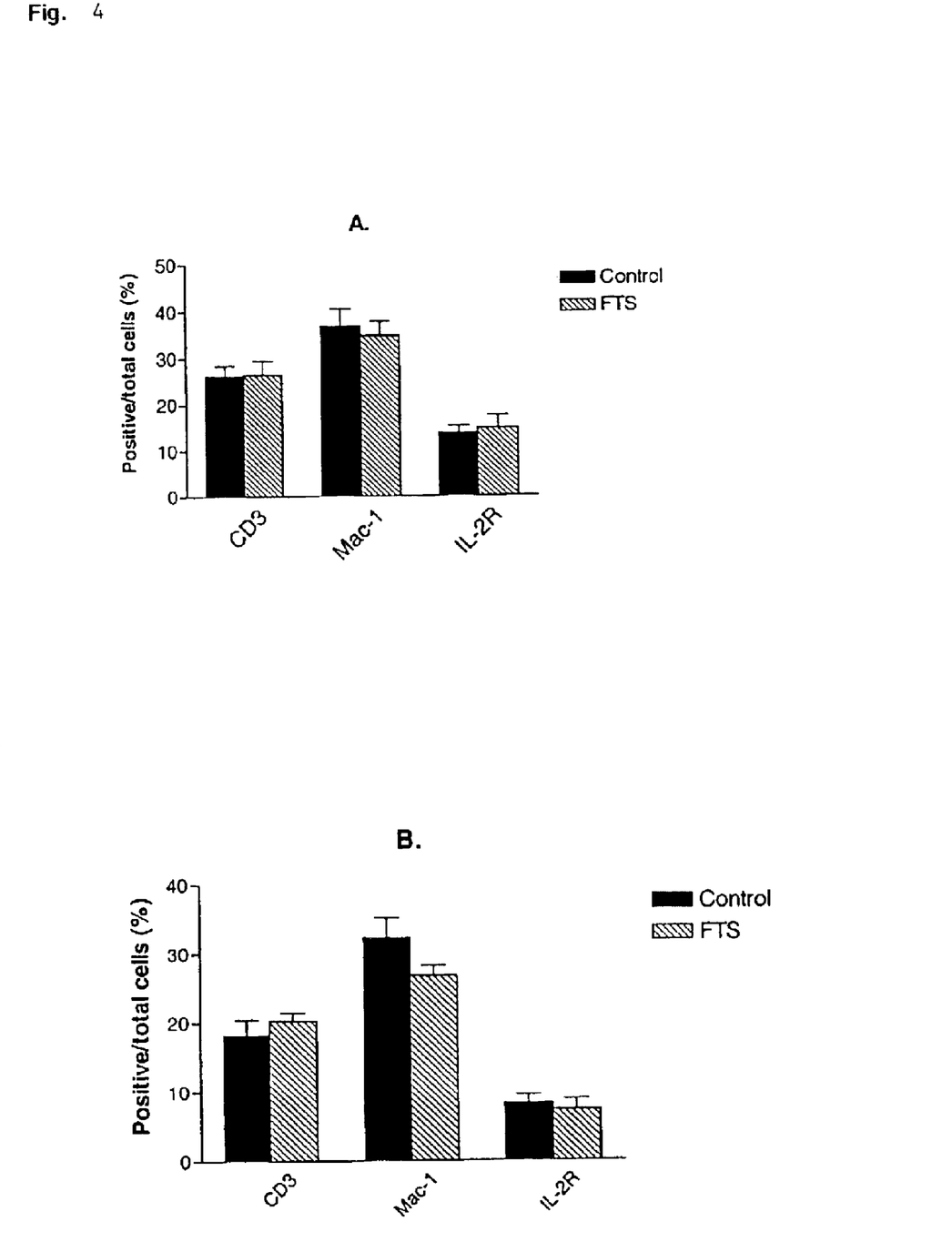
FIGS. 4A and 4B are bar graphs showing that treatment with FTS does not alter atherosclerotic plaque composition based upon staining with monoclonal antibodies to CD3, Mac-1 and IL-2-R, using plaque-positive cells from fatty streaks (FIG. 4A) and advanced lesions (FIG. 4B).
Figure 5:
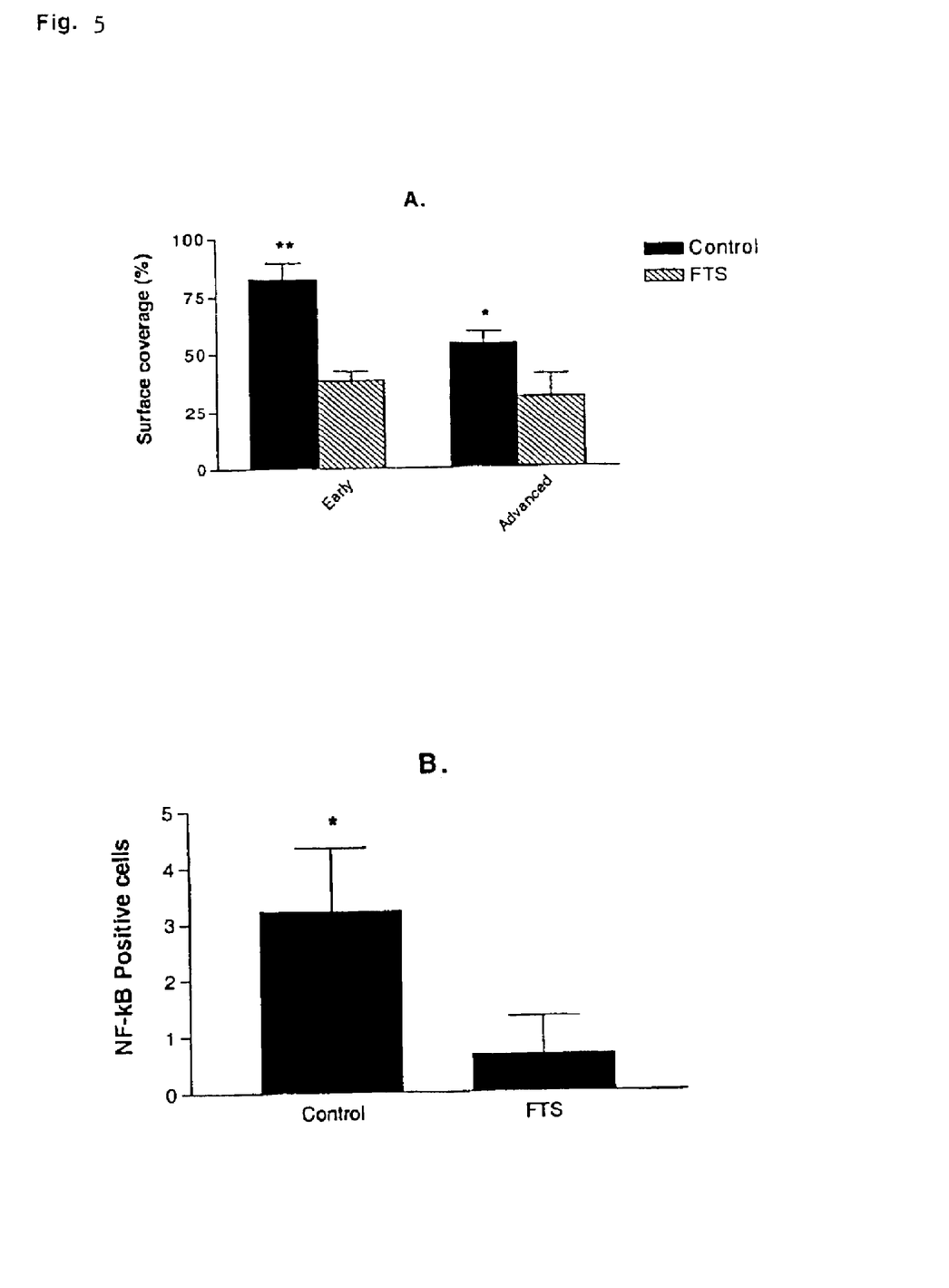
FIG. 5A is a bar graph showing that FTS reduces VCAM-1 expression in atherosclerotic plaques in aortic sinus early and advanced lesions compared to control mice.
FIG. 5B is a bar graph showing that FTS reduces NF-kB expression in atherosclerotic plaques in aortic lesions obtained from FTS compared to control mice.

To investigate whether reduction in atherosclerotic lesion size induced by FTS, altered plaque composition, we evaluated the relative density of macrophages, total lymphocytes and activated (IL–2R+) lymphocytes. FTS treatment in both experiments did not appear to influence the relative numbers of macrophages and lymphocytes (FIGS. 4A and B). We then evaluated the relative expression of a key adhesion molecule (VCAM-1) in plaques following FTS treatment by morphometry. Administration of FTS considerably reduced VCAM-1 expression in fatty streaks of mice from the 6-week treatment schedule as compared with control (a 53% reduction; FIG. 5A). A similar, though less pronounced effect of FTS was evident on VCAM-1 expression in more advanced plaques (a 43% reduction by FTS; FIG. 5A; photo not shown).

As NF-kB is a transcription factor known to trigger VCAM-1 expression. We sought to evaluate its relative abundance in the plaques and found that NF-kB positive cells were reduced in FTS treated lesions in comparison with controls (FIG. 5B). The numbers of NF-kB expressing cells were too low to obtain a meaningful count in the first experiment.

Discussion

The results demonstrate the efficacy of functional Ras inhibition by FTS of various Ras activity associated with atherosclerotic plaque initiation and progression in murine atherosclerosis. The effect was obtained in early fatty streaks, and in more advanced plaques induced by high fat diet supplementation.

It has been suggested that ras mutations are present in samples from human atherosclerotic plaques (8). Ras has been shown to activate NF-kB (15), a transcription factor that is known to trigger production and expression of adhesion molecules that are essential to the initiation of atherosclerotic plaques. NF-kB has recently been shown to be expressed within atherosclerotic plaques (16). We have shown here, that VCAM-1 expression within the plaques is reduced following anti-Ras treatment. We have also shown that NF-kB positive cells are reduced in lesions from FTS treatment supporting our belief that interference with Ras activation and signaling results in attenuation of NF-kB mediated induction of adhesion molecules. Our observation that VCAM-1 plaque coverage was reduced to a larger extent by FTS in early plaques in comparison with more advanced plaques is consistent with the relatively more important role of VCAM-1 in early atherosclerotic lesions.

We have also found the FTS treatment reduced Ras-GTP content by approximately 40%, as compared with control aortas. As homogenates from the aortas contain a heterogenous population of cells, only part of which are actively proliferating, the effect of FTS is apparently not complete. Yet, it is likely that Ras inhibition in active Ras-expressing cells within the atheroma, would be significantly more pronounced. Total Ras protein did not differ between FTS and control treated aortas. This finding can also be explained by the mixed population of cells within the plaques, not all of which express Ras in a similar level. Thus, FTS treatment was sufficient to inhibit active Ras in the aortas without affecting total protein content. This lack of global effect on Ras protein may well explain the lack of side effects that would be expected to result from inhibition of such a key signaling protein.

Atherogenesis is a process in which the immune system appears to take an active part (1,2). Accordingly, activated lymphocytes have been detected in human (17) and murine (18) plaques, sometimes even preceding the infiltrating lipid-laden macrophages. Ras protein expression has been shown to be involved in regulating lymphocyte activation (19). Thus, interference with lymphocyte activation by anti-Ras treatment could be a potential beneficial anti-atherogenic mechanism. Herein, we failed to notice differences in lymphocyte density within atherosclerotic plaques between FTS and control treated mice, nor did we find evidence that activation markers were reduced as a result anti-Ras therapy. However, systemic immune responses towards oxLDL, which have been associated with development of atherogenesis, were indeed altered. Accordingly, proliferative response of splenocytes from FTS treated mice to oxLDL were reduced as compared with responses recorded from control lymphoyctes. Moreover, antibodies to oxLDL were also diminished by FTS treatment. We believe that these findings demonstrate that attenuation of immune reactions resulting from oxidative stress is mediated by interference with Ras activation, which contributes to the anti-atherogenic effect.

The atherosclerotic process entails a proliferative phenotype, involving, apart from lymphocytes and macrophages, also smooth muscle cells, which occupy lesions that are relatively more advanced (1). Approaches designed to block Ras-mediated smooth muscle cell proliferation and migration have been successful in several in-vitro studies (20). Moreover, studies employing gene delivery of dominant negative forms of ras have been shown effective in suppressing neointimal formation after experimental carotid injury (21–22). We believe that FTS induced suppression of atherosclerotic lesions by altering the proliferative phenotype of atherosclerotic lesions. Additionally, FTS inhibits cell migration (14), a property that may be relevant to atherosclerosis suppression that involves recruitment of monocyte and lymphocytes followed by smooth muscle cells and fibroblasts.

FTS and analogs thereof (as represented by formula I) bear some advantages over other inhibitors that were designed to inhibit Ras (9,23). FTS is the only compound that affects all isoforms of activated Ras, namely activated H-, K-, and N-Ras (9). Other compounds such as farnesyltransferase inhibitors, for example, are good inhibitors of H-Ras but not of other Ras isoforms. This property coupled with the lack of FTS toxicity in animal models make FTS an attractive potential drug, particularly for the treatment of multifactorial disorders such as atherosclerosis. It is more probable that not that more than one Ras isoform (in diverse cell types) is activated during the atherosclerotic process. Our experiments lend support for a mechanism-based action of FTS in atherosclerosis as expected from its in vitro inhibition of Ras and its functions (9). First, they demonstrate that the in vivo effects of FTS are manifested in the reduction in the contents of active, GTP-bound Ras, in the atherosclerotic aortas. Second, they demonstrate the reduced proliferative response of splenocytes from FTS-treated mice to oxLDL. Third, they show the reduced levels of antibodies to oxLDL in the FTS treated apoE mice, with no effect of antibody class distribution. These observations support the contention that FTS, at the doses employed in the current study, would induce functional Ras blockade in vivo.

In conclusion, FTS, a functional Ras inhibitor, has been shown to suppress early and more advanced atherosclerosis. The effects brought about by FTS are probably multifactorial. In certain embodiments, it is advantageous to employ the Ras antagonist in combination with lipid lowering agents.

References
1. Ross, R., N. Eng. J. Med. 340:115–126 (1999).
2. Libby et al. Lab. Invest. 64:5–11 (1991).
3. Boguski et al. Nature (London) 366:643–654 (1993).
4. Rebollo et al. Blood 94:2971–2980 (1999).
5. Lange-Carter et al. Science 265:1458–1461 (1994).
6. Li et al. Mol. Cell. Biol. 6:5947–54 (1996).
7. Chatterjee et al. Glycobiology 7:703–710 (1997).
8. Kiaris et al. Atherosclerosis 125:47–51 (1996).
9. Kloog et al. Drugs 8:2121–2140 (1999).
10. Marom et al. J. Biol. Chem. 270:22263–22270 (1995).
11. Haklai et al. Biochemistry 37:1306–1314 (1998).
12. Weisz et al. Oncogene 18:2579–2588 (1999).
13. Jansen et al. Proc. Natl. Acad. Sci. U.S.A 96:14019–14024 (1999).
14. Reif et al. J. Hepatol. 31:1053–1061 (1999).
15. Finco et al. J. Biol. Chem. 272:24113–6 (1997).
16. Hajra et al. Proc. Natl. Acad. Sci. U.S.A. 97:9052–9057 (2000).
17. Hansson et al. Am. J. Pathol. 135:169–175 (1989).
18. Roselaar et al. Arteriscler. Thromb. Vasc. Biol. 16:1013–1018 (1996).
19. Genot et al. Curr. Opin. Immunol. 12:289–294 (2000).
20. Kouchi et al. Biochem. Biophys. Res. Commun. 264:915–920 (2000).
21. Ueno et al. Thromb. Vase. Biol. 17:898–904 (1997).
22. Indolfi et al. Nat. Med. 1:541–545 (1995).
23. Reuter et al. Blood 96:1655–1669 (2000).
24. Plump et al. Cell 71:343–353 (1992).
25. Zhang et al. Science 258:468–471 (1992).
26. George et al. Circ. Res. 86:203–1210 (2000).
27. George et al. Circulation 15:1108–1115 (1998).
28. Herman et al. J. Biol. Chem. 270:11654–11661 (1995).
29. George et al. Atherosclerosis 138:147–152 (2000).

EXAMPLE 2

The Effect of FTS on Intimal Hyperplasia in a Model of Carotid Balloon Injury in the Rat The aim of this experiment was to investigate the effect of FTS on intimal hyperplasia in a rat carotid balloon injury, as an indication of whether FTS can ameliorate restenosis by reducing smooth muscle cell proliferation and migration. The results indicate that FTS appears to be a potent inhibitor of intimal hyperplasia.

Atherosclerosis and restenosis are two processes that involve cellular proliferation that eventually lead to functional narrowing of blood vessels causing considerable morbidity and mortality (1–4). The formation of neointimal hyperplasia following balloon denudation is thought to involve proliferation and migration of medial smooth muscle cells or modified adventitial fibroblasts (4, 5, 6, 7). In recent years, evidence has also accumulated pointing towards the involvement of the immune system in atherosclerosis and restenosis, as manifested by the local presence of activated T lymphocytes (3, 4) and elevation of inflammatory markers such as CRP, IL-6 and other markers (8–10).

The long-term effectiveness of percutaneous balloon coronary angioplasty (PTCA) and stent implantation is still largely limited due to the occurrence of late lumen loss following intimal thickening. Although several experimental strategies have provided some success in reducing intimal thickening in animals, clinical trials in humans performed so far failed to achieve significant improvement (10–17). Effective clinical utility in reducing the rate of restenosis was recently shown only for intracoronary radiation therapy (18–19).

Methods

Animals

Male Wistar rats 6 weeks old (weighing 250–280 gr). The animals were purchased from the Tel Aviv University and maintained at the local animal house.

Study Design

Group A: Four rats received daily intraperitoneal injections of FTS (5 mg/Kg) starting from the day of injury induction until sacrifice, 14 days later.

Group B: Four rats received daily intraperitoneal injections of control vehicle starting from the day of injury induction until sacrifice, 14 days later.

Rat Carotid Injury Method

Animals were anesthetized by intraperitoneal injection of Ketamin (80 mg/Kg) and Xylazine (5 mg/Kg). Endothelial denudation and vascular injury was achieved in the left common carotid artery, as described (6). Briefly, a balloon catheter (2F Fogarty) was passed through the external carotid into the aorta; the balloon was inflated with sufficient water to distend the common carotid artery and then pulled back to the external carotid. This procedure was repeated three times, and then the catheter was removed. After 14 days, the animals were sacrificed and the right and left carotid arteries were taken out and fixed in 4% paraformaldehyde until embedding in Paraffin. The arteries were cut in 10 um sections and stained with H&E and computer-assisted morphometric analyses were performed. The tested parameters were: intimal area, medial area, intimal/medial ratio and lumen area. Additionally, the %CSAN-N (% cross sectional area neointimal-neointamal) was calculated [IEL area-Lumen area]×100/IEL (a measure of the degree to which the IEL area is reduced by neointimal hyperplasia with greater normalization of the effect of changes in vessel wall size. Vasular remodeling process were further evaluated by computing the amount of plaque relative to the EEL (external elastic lamina) area.

Immunohistochemistry

Paraffin fixed sections (10 um) were stained with a Pan Ras antibody.

Statistical Analysis

Results of all parameters were computed employing 2 tailed student's t-test. Results are presented as means±SEM. p<0.0.5 was considered significant.

Results

Intimal area was significantly reduced (76%) in rats treated with FTS (0.38 mm$^2$) in comparison with control treated animals (1.61 mm$^2$; p=0.02). FTS did not significantly influence medial area (0.91 mm$^2$) in the treated group as compared with the control group (1.2±0.14 mm$^2$). Intimal to medial ratio was significantly reduced in FTS treated rats (0.49±0.19 mm$^2$) as compared with controls (1.29±0.20 mm$^2$; p=0.02). The luminal area was significantly increased in FTS-treated rats (1.45±0.34 mm$^2$) in comparison with control animals (2.30±0.32; p=0.015). %CSAN-N in the FTS rats was significantly reduced (14.5±4.3%) in comparison with control treated animals (52.4±7.4%; p=0.004). Increased amount of neointimal proliferation was not associated with larger EEL area. Immunostainable Ras was abundantly present in the neointimal cells and only low expression was evident in the media and adventitia.

Conclusions

FTS appears as a potent inhibitor of intimal hyperplasia induced by carotid balloon injury in the rat. Increased patency of the vessel lumen by FTS was mainly due to prevention of neointimal proliferation and not due to the vessel wall remodeling processes. Thus, the onset of restenosis may be inhibited, or restenosis may be treated by coating or otherwise contacting the stent with the Ras antagonist prior to deployment of the stent, systemic treatment with the Ras antagonist following PTCA or administration of the Ras antagonist following heart transplantation or coronary arterial bypass graft to inhibit accelerated atherosclerosis.

References

1. Liu et al. Circulation 79:1374–1387 (1989).
2. Fuster et al. N. Engl. J. Med. 236:242–250 (1992).
3. Libby et al. Circulation 86 (Suppl.):III47–III52 (1992).
4. Ross, Nature (Lond.). 362:01–809 (1993).
5. Hanke et al. Circulation Res. 67:651–659 (1990).
6. Shi et al. Circulation 94:1655–1664 (1996).
7. Andersen, Circulation 93:1716–1724 (1996).
8. Ridker et al, Engl. J. Med. 336:973–979 (1997).
9. Ridker et al. Circulation 98:31–733 (1998).
10. Koeing, Eur. Heart J. Suppl. 1:T19–T26 (1999).
11. Clowes et al. Lab Invest. 49:327–334 (1983).
12. Kaltenbach et al. Eur. Heart J. 6:276–281 (1985).
13. Nobuyoshi et al. J. Am. Coll. Cardiol. 12:616–623 (1988).
14. RITA Trial Participants Lancet. 341:573–580 (1993).
15. Califf et al. J. Am. Coll. Cardiol. 17:B–133B (1991).
16. Popma et al. Circulation 84:1426–1436 (1991).
17. Franklin et al. Coronary Artery Dis. 4:232–242 (1993).
18. Teirstein et al. N. Eng. J. Med 336:1697–1703 (1997).
19. Condado et al. Circulation 96:727–732 (1997).

All patent and non-patent publications cited in this specification are indicative of the level of skill of those skilled in the art to which this invention pertains. All these publications are herein incorporated by reference to the same extent as if each individual publication or patent application were specificaly and individually indicated to be incorporated by reference.

Various modifications of the invention described herein will become apparent to those skilled in the art. Such modifications are intended to fall within the scope of the appending claims.

What is claimed is:

1. A method of treating a mammal suffering from or at risk of vascular injury, comprising: administering to a patient a Ras antagonist in an mount effective to treat the mammal, wherein the Ras antagonist is represented by the formula wherein:
$R^1$ represents farnesyl, geranyl or geranyl-geranyl;
Z represents C—$R^6$ or N;
$R^2$ represents H, CN, the groups $COOR^7$, $SO_3R^7$, $CONR^7R^8$, COOM, $SO_3M$ and $SO_2NR^7R^8$, wherein $R^7$ and $R^8$ are each independently hydrogen, alkyl or alkenyl, and wherein M is a cation;
$R^3$, $R^4$, $R^5$ and $R^6$ are each independently hydrogen, carboxyl, alkyl, alkenyl, aminoalkyl, nitroalkyl, nitro, halo, amino, mono- or di-alkylamino, mercapto, mercaptoalkyl, axido, or thiocyanato;
X represents O, S, SO, $SO_2$, NH or Se; and
the quaternary ammonium salts and N-oxides of the compounds of said formula when Z is N.

2. The method of claim 1 wherein the Ras antagonist is farnesyl-thiosalicyclic acid (FTS).
3. The method of claim 1 wherein the Ras antagonist is 2-chloro-5-farnesylaminobenzoic acid (NFCB).
4. The method of claim 1 wherein the Ras antagonist is farnesyl thionicotinic acid (FTN).
5. The method of claim 1 wherein the Ras antagonist is 5-fluoro-FTS.
6. The method of claim 1 wherein the Ras antagonist is 5-chloro-FTS.
7. The method of claim 1 wherein the Ras antagonist is 4-chloro-FTS.
8. The method of claim 1 wherein the Ras antagonist is S-farnesyl-thiosalicylic acid methyl ester.
9. The method of claim 1 wherein the Ras antagonist is administered parenterally.
10. The method of claim 1 wherein the Ras antagonist is administered orally.
11. The method of claim 1 wherein the Ras antagonist is administered prophylactically.
12. The method of claim 1 wherein the Ras antagonist is administered in a formulation containing a cyclodextrin.
13. The method of claim 1 wherein the Ras is activated Ras.
14. The method of claim 1 wherein the vascular injury is post-angioplasty restenosis.
15. The method of claim 14 wherein the Ras antagonist is administered prophylactically.
16. The method of claim 1 wherein the vascular injury is atherosclerosis.
17. The method of claim 1 wherein the Ras antagonist is represented by the formula wherein
$R^1$ represents farnesyl, geranyl or geranyl-geranyl;
Z represents C—$R^6$;
$R^2$ represents H, CN, the groups $COOR^7$, $SO_3R^7$, $CONR^7R^8$, COOM, $SO_3M$ and $SO_2NR^7R^8$, wherein $R^7$ and $R^8$ are each independently hydrogen, alkyl or alkenyl, and wherein M is a cation;
$R^3$, $R^4$, $R^5$ and $R^6$ are each independently hydrogen, carboxyl, alkyl, akenyl, aminoalkyl, nitroalkyl, nitro, halo, amino, mono- or di-alkylamino, mercapto, mercaptoalkyl, axido, or thiocyanato; and
X represents O, S, SO, $SO_2$, NH or Se.

18. The method of claim 1 wherein the Ras antagonist is represented by the formula wherein
$R^1$ represents farnesyl, geranyl or geranyl-geranyl;
Z represents C—$R^6$;
$R^2$ represents CN, the groups $COOR^7$, $SO_3R^7$, $CONR^7R^8$, COOM, $SO_3M$ and $SO_2NR^7R^8$, wherein $R^7$ and $R^8$ are each independently hydrogen alkyl or alkenyl, and wherein M is a cation;
$R^3$, $R^4$, $R^5$ and $R^6$ are each independently hydrogen, carboxyl, alkyl, alkenyl, aminoalkyl, nitroalkyl, nitro, halo, amino, mono- or di-alkylamino, mercapto, mercaptoalkyl, axido, or thiocyanato; and
X represents O, S, SO, $SO_2$, NH or Se.

19. The method of claim 2, wherein the vascular injury is atherosclerosis.
20. The method of claim 2, wherein the vascular injury is post-angioplasty restenosis.
21. The method of claim 2, wherein the Ras antagonist is administered prophylactically.
22. The method of claim 2, 19 or 20 wherein the Ras antagonist is administered orally.
23. The method of claim 5, wherein the vascular injury is atherosclerosis.
24. The method of claim 5, wherein the vascular injury is post-angioplasty restenosis.
25. The method of claim 5, wherein the Ras antagonist is administered prophylactically.
26. The method of claim 5, 23 or 24 wherein the Ras antagonist is administered orally.
27. The method of claim 6, wherein the vascular injury is atherosclerosis.
28. The method of claim 6, wherein the vascular injury is post-angioplasty restenosis.
29. The method of claim 6, wherein the Ras antagonist is administered prophylactically.
30. The method of claim 6, 27 or 28 wherein the Ras antagonist is administered orally.
31. The method of claim 7, wherein the vascular injury is atherosclerosis.
32. The method of claim 7, wherein the vascular injury is post-angioplasty restenosis.
33. The method of claim 7, wherein the Ras antagonist is administered prophylactically.
34. The method of claim 7, 31 or 32 wherein the Ras antagonist is administered orally.
35. The method of claim 8, wherein the vascular injury is atherosclerosis.
36. The method of claim 8, wherein the vascular injury is post-angioplasty restenosis.

37. The method of claim 8, wherein the Ras antagonist is administered prophylactically.

38. The method of claim 8, 35, or 36 wherein the Ras antagonist is administered orally.

39. The method of any one of claims 1–16, wherein the mammal is a human.

40. The method of any one of claims 17–21, wherein the mammal is human.

41. The method of claim 22, wherein the mammal is a human.

42. The method of any one of claims 23–25, wherein the mammal is a human.

43. The method of claim 26, wherein he mammal is a human.

44. The method of any one of claims 27–29, wherein the mammal is a human.

45. The method of claim 30, wherein he mammal is a human.

46. The method of any one of claims 31–33, wherein the mammal is a human.

47. The method of claim 34, wherein he mammal is a human.

48. The method of any one of claims 35–37, wherein the mammal is a human.

49. The method of claim 38, wherein the mammal is a human.

* * * * *

UNITED STATES PATENT AND TRADEMARK OFFICE
CERTIFICATE OF CORRECTION

PATENT NO. : 6,946,485 B2
DATED : September 20, 2005
INVENTOR(S) : Yoel Kloog et al.

It is certified that error appears in the above-identified patent and that said Letters Patent is hereby corrected as shown below:

Column 1,
Line 48, "subtypes," should read -- subtypes --.

Column 4,
Line 39, "agrowing" should read -- a growing --.

Column 6,
Line 7, insert the following:
-- These compounds are the subject of U.S. Patent 5,705,528. Methods of synthesizing the compounds are also disclosed therein. --.

Column 8,
Line 54, "water," should read -- water --.

Column 11,
Line 32, "were" should read -- was --.

Column 13,
Line 36, "were" should read -- was --.
Lien 36, "make" should read -- makes --.

Column 15,
Line 57, "process" should read -- processes --.

Column 18,
Line 25, "hydrogen" should read -- hydrogen, --.

Column 19,
Line 13, "he" should read -- the --.

UNITED STATES PATENT AND TRADEMARK OFFICE
CERTIFICATE OF CORRECTION

PATENT NO. : 6,946,485 B2
DATED : September 20, 2005
INVENTOR(S) : Yoel Kloog et al.

It is certified that error appears in the above-identified patent and that said Letters Patent is hereby corrected as shown below:

Column 20,
Lines 3 and 7, "he" should read -- the --.

Signed and Sealed this

Tenth Day of January, 2006

JON W. DUDAS
*Director of the United States Patent and Trademark Office*